US009539358B2

(12) United States Patent
Wang et al.

(10) Patent No.: US 9,539,358 B2
(45) Date of Patent: *Jan. 10, 2017

(54) OXIDIZED REGENERATED CELLULOSE HEMOSTATIC POWDERS AND METHODS OF MAKING

(71) Applicant: Ethicon, Inc., Somerville, NJ (US)

(72) Inventors: Yi-Lan Wang, Belle Mead, NJ (US); Guanghui Zhang, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/333,697

(22) Filed: Jul. 17, 2014

(65) Prior Publication Data

US 2014/0329769 A1  Nov. 6, 2014

Related U.S. Application Data

(62) Division of application No. 13/480,842, filed on May 25, 2012, now Pat. No. 8,815,832.

(51) Int. Cl.
  *A61L 26/00* (2006.01)
(52) U.S. Cl.
  CPC .......... *A61L 26/0023* (2013.01); *A61L 26/009* (2013.01); *A61L 26/0061* (2013.01); *A61L 26/0066* (2013.01); *A61L 2300/404* (2013.01); *A61L 2300/418* (2013.01); *A61L 2400/04* (2013.01); *Y10T 428/2982* (2015.01)
(58) Field of Classification Search
  None
  See application file for complete search history.

(56) References Cited

U.S. PATENT DOCUMENTS

| | | | |
|---|---|---|---|
| 3,364,200 | A | 1/1968 | Ashton et al. |
| 4,626,253 | A | 12/1986 | Broadnax, Jr. |
| 5,180,398 | A | 1/1993 | Boardman et al. |
| 5,696,191 | A | 12/1997 | Nohr et al. |
| 6,225,461 | B1 | 5/2001 | Akimoto et al. |
| 6,309,454 | B1 | 10/2001 | Harvey et al. |
| 6,627,749 | B1 | 9/2003 | Kumar |
| 6,652,840 | B1 | 11/2003 | Prevendar |
| 2004/0005350 | A1 | 1/2004 | Looney et al. |
| 2006/0233869 | A1 | 10/2006 | Looney et al. |
| 2007/0141156 | A1* | 6/2007 | Herzberg et al. ............ 424/486 |
| 2008/0027365 | A1 | 1/2008 | Huey |

FOREIGN PATENT DOCUMENTS

| | | |
|---|---|---|
| CN | 1575821 | 2/2005 |
| CN | 101365460 | 2/2009 |
| CN | 102190736 | 9/2011 |
| EP | 1323436 | 7/2003 |
| WO | WO 01/24841 | 4/2001 |
| WO | WO 2007/076415 | 7/2007 |

OTHER PUBLICATIONS

Dallaire, Clemex intelligent microscopy, Shape Detail and Volume Calculations in Micronized Powders, Feb. 2008.*
Netafim Mesh vs. Micron Comparison Chart, downloaded from the internet Jan. 29, 2016.*
Cullen, B. et al. "The role of oxidised regenerated cellulose/collagen in chronic wound repair and its potential mechanism of action" *The International Journal of Biochemistry & Cell Biology* (2002) vol. 34 pp. 1544-1556.
Rajkhowa, R. et al. "Ultra-fine silk powder preparation through rotary and ball milling" *Powder Technology* (2008) vol. 185 pp. 87-95.
Howsmon, et al "The Ball-Milling of Cellulose Fibers and Recrystallization Effects" *Journal of Applied Polymer Science* (1959) vol. 1 Issue 3 pp. 313-322.
Yasnitskii, B.G. et al., "Oxycelodex, a New Hemostatic Preparation" *Khimiko-farmatsevticheskii Zhurnal* (1983) vol. 18, No. 4 pp. 506-508.
Avolio, R et al., "A multitechnique approach to assess the effect of ball milling on cellulose, Carbohydrate Polymers," *Applied Science Publishers*, LTD. Barking, GB, vol. 87, No. 1, Jul. 25, 2011, pp. 265-273.
Yasnitskii, B.G. et al., "Oxycelodex, A New Hemostatic Preparation" Khimiko farmatsevticheskii Zhurnal (1983) vol. 18, No. 4 pp. 279-281.
PCT Search Report PCT/US2013/042149 dated Jul. 2, 2013.
International Preliminary Report on Patentability re: PCT/US2013/042149 dated Nov. 25, 2014.

* cited by examiner

*Primary Examiner* — Layla Berry
(74) *Attorney, Agent, or Firm* — David R. Crichton; Leo B. Kriksunov

(57) ABSTRACT

The present invention is directed to hemostatic material containing compacted ORC powder comprising particles having an average aspect ratio from about 1 to about 18, wherein said compacted ORC powder have preferably been processed in a compaction device, such as a ball milled ORC powder. The present invention further relates to methods of making the hemostatic material and a method of treating a wound by applying the hemostatic powder onto and/or into the wound of a patient.

9 Claims, 8 Drawing Sheets

OXIDIZED REGENERATED CELLULOSE HEMOSTATIC POWDERS AND METHODS OF MAKING

FIELD OF THE INVENTION

The present invention is directed to resorbable hemostatic powders with improved efficacy, particularly compacted powders made of oxidized regenerated cellulose, and to methods for manufacturing such powders.

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin, collagen, chitin, chitosan, etc. To improve the hemostatic performance, scaffolds based on the above materials can be combined with biologically-derived clotting factors, such as thrombin and fibrinogen.

The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. A number of methods for forming various types of hemostats based on oxidized cellulose materials are known, whether made in powder, woven, non-woven, knit, and other forms. Currently utilized hemostatic wound dressings include knitted or non-woven fabrics comprising oxidized regenerated cellulose (ORC), which is oxidized cellulose with increased homogeneity of the cellulose fiber. Examples of such hemostatic wound dressings commercially available include SURGICEL® resorbable hemostat; SURGICEL® NU-KNIT® resorbable hemostat; SURGICEL® FIBRILLAR resorbable hemostat, and SURGICEL® SNoW™ resorbable hemostat; all available from Johnson & Johnson Wound Management Worldwide, a division of Ethicon, Inc., Somerville, N.J., a Johnson & Johnson Company. Other examples of commercial resorbable hemostats containing oxidized cellulose include GelitaCel® resorbable cellulose surgical dressing from Gelita Medical BV, Amsterdam, The Netherlands. The commercially available oxidized cellulose hemostats noted above are knitted or nonwoven fabrics having a porous structure for providing hemostasis.

U.S. Pat. No. 3,364,200 to Ashton and Moser describes a resorbable, surgical hemostat in the form of pledgets of integrated oxidized cellulose staple fibers.

Published U.S. Patent Application Publication 2008/0027365 to Huey describes an apparatus for promoting hemostasis utilizing oxidized cellulose in the form of a compressible, shapeable mass that is formed into a sheet for placement on a bleed site and further having a sleeve in a form of a tubular shell dimensioned to receive a limb.

Published U.S. Patent Application Publication 2004/0005350 to Looney et al. discloses hemostatic wound dressings utilizing a fibrous fabric substrate made from carboxylic-oxidized cellulose and containing a porous, polymeric matrix homogeneously distributed through the fabric and made of a biocompatible, water-soluble or water-swellable cellulose polymer, wherein the fabric contains about 3 percent by weight or more of water-soluble oligosaccharides.

Patent publication WO 2007/076415 by Herzberg et al. and entitled "COMPOSITIONS AND METHODS FOR PREVENTING OR REDUCING POSTOPERATIVE ILEUS AND GASTRIC STASIS", discloses milling of ORC, particularly cryogenic milling, using a cutting blade of a motor-driven mill.

An article titled "The Ball-Milling of Cellulose Fibers and Recrystallization Effects", Journal of Applied Polymer Science, Volume 1 Issue 3, Pages 313-322, (1959) by Howsmon and Marchessault, reports results of a study of the effect of fine structure on the decrystallization process which results from the ball-milling of cellulose. The rate of decrystallization is sensitive to the type of fine structure and is accelerated by the presence of moisture. The extent of chain degradation was greater in air atmosphere than in carbon dioxide, suggesting that mechanically induced free radical degradation occurs along with other chain-breaking processes. A study of the density and moisture regain of the samples after various times of milling showed that a linear relation between regain and density held over the entire range studied. The relation was the same for native and regenerated cellulose. The process of recrystallization of the ball-milled samples was studied under various conditions and compared to the hydrolytically induced recrystallization of rayons. The reference discloses effect of fine structure on the decrystallization process which results from the ball-milling of cellulose fibers.

U.S. Pat. No. 6,627,749 discloses a process for grinding oxidized cellulose using a pestle and mortar or in a ball mill or any other conventional laboratory grinder. It further discloses that when cotton linter sheet is used as the starting cellulose source, the fiber length of the product decreases with increasing reaction time. When ball-milled, the long fibrous structures of the product turn into smaller fibers, to loosely-packed spherical aggregates. No significant change in the crystallinity of these samples occurs as a result of ball milling. The reference discloses long fibrous oxidized cellulose ball milled to form small fibers or loosely packed spherical aggregates.

Other related references include: U.S. Pat. No. 6,309,454, Freeze-dried composite materials and processes for the production thereof; U.S. Pat. No. 5,696,191; U.S. Pat. No. 6,627,749; U.S. Pat. No. 6,225,461 to Kyoko et al.; PCT patent publication WO2001/024841 A1, Compositions for the Treatment of Wound Contracture; and European patent publication EP1,323,436 to Dae Sik et al.

Other related references include: An article titled "The role of oxidized regenerated cellulose/collagen in chronic wound repair and its potential mechanism of action", The International Journal of Biochemistry & Cell Biology 34 (2002) 1544-1556, Breda Cullen et al.; an article by Rangam et al. teaching methods of making silk powders through milling processes [Powder Technology 185(2008), p 87-95]; an article by Yasnitskii et al., Oxycelodex, a new hemostatic preparation, Pharmaceutical Chemistry Journal, 18, 506-5;

discloses an Oxycelodex paste that consists of two components, oxidized cellulose powder and a 20% aqueous solution of dextran.

U.S. Patent Application 2006/0233869 to Looney et al. discloses using a chopping/shredding process to make ORC micro-fibers from ORC fabrics. The rod-like shaped fibers had sizes which ranged from about 35 to 4350 micrometers.

SUMMARY OF THE INVENTION

The present invention is directed to a hemostatic material comprising a compacted ORC powder that has particles with an average aspect ratio from about 1 to about 18. The compacted ORC powder is preferably made by ball milling. More particularly, the compacted ORC powder can be roller compaction processed ORC powder or hammer mill processed ORC powder. The hemostatic material preferably has a tapped density of at least 0.45 g/cm$^3$, and/or a flowability of at least 7.5 cm/s; and/or an average particle size of 1.75 microns to 116 microns with a median size of 36 microns. In one embodiment, the hemostatic material is a powder with particles having average aspect ratio from about 1 to about 5; a tapped density of at least 0.67 g/cm$^3$ and flowability of at least 70.

In one embodiment, the hemostatic material further includes an additive, such as carboxymethyl cellulose (CMC) or other polysaccharides, calcium salt, anti-infective agent, hemostasis promoting agent, gelatin, collagen, or combinations thereof.

In another embodiment, the hemostatic material is in the form of a paste that comprises the hemostatic materials of described above and a saline solution. The paste preferably has a viscosity greater than 10000 Pa-s at room temperature.

In another embodiment, the present invention is directed to a method of making the hemostatic materials described above by compacting an ORC-based material into a powder, until said powder reaches an aspect ratio of from about 1 to about 18. The ORC-based material can be ORC in fabric form, ORC in non-woven form, or a shredded ORC material. In one embodiment, the compacting is performed by ball milling. In another embodiment, the compacting is performed by roller compaction or by hammer milling. In yet another embodiment, the ORC-based material can be combined with an additive, such as CMC, calcium salt, anti-infective agent, hemostasis promoting agent, gelatin, collagen, saline, or combinations thereof.

In another embodiment, the present invention is directed to a method of treating a wound by applying hemostatic powders described above onto and/or into the wound of a patient.

DETAILED DESCRIPTION

Figure 1:
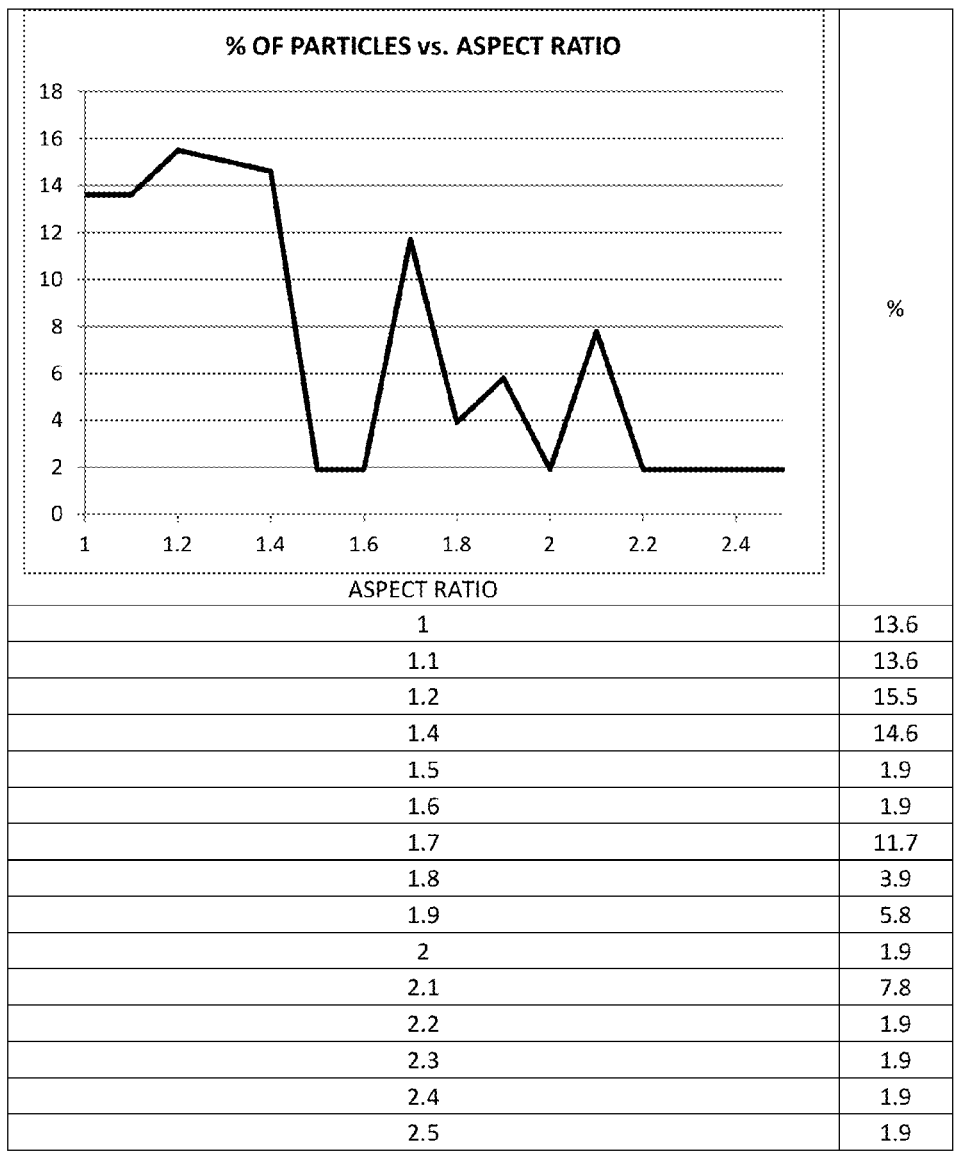
FIG. 1 is a graph of particle size distribution of ball milled material as measured by dynamic light scattering.

The inventors discovered a process for making compacted ORC powder having specific properties from ORC-based materials or from pre-shredded ORC-based materials, whereby the resulting powder can be used for various surgical and wound healing topical applications, such as anti-adhesion barriers, hemostats, tissue sealants, etc. Oxidized regenerated cellulose materials which are used as a starting material for making compacted ORC powder of the present invention are known and commercially available. The materials include absorbable woven or knitted fabric or non-woven materials comprising oxidized polysaccharides, in particular oxidized cellulose and the neutralized derivatives thereof. For example, the cellulose may be carboxylic-oxidized or aldehyde-oxidized cellulose. More preferably, oxidized regenerated polysaccharides including, but without limitation, oxidized regenerated cellulose may be used. Oxidized regenerated cellulose is preferred due to its higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents each of which is hereby incorporated by reference as if set forth in its entirety. Examples of materials that may be utilized as the include, but are not limited to, INTERCEED® absorbable adhesion barrier, SURGICEL® absorbable hemostat, SURGICEL® NU-KNIT® absorbable hemostat, SURGICEL® FIBRILLAR absorbable hemostat, or SURGICEL® SNoW™ absorbable hemostat (each available from Johnson & Johnson Wound Management Worldwide, a division of Ethicon, Inc., Somerville, N.J.).

Due to high tapped density and low aspect ratio of powders of the present invention, the resulting ORC powders can perform as a hemostat in either a paste or powder form with superior hemostatic properties and good tissue conformability and flowability. In addition, the ORC materials can be physically incorporated with other agents and biopolymers to improve adherence to tissues, sealing properties, and/or anti-adhesions properties.

In one aspect of the present invention, there is provided a method for making, low aspect ratio (1-20, such as 1.5-19) particulates which are compacted into high tapped density powders, with tapped density ranging from about 0.35 to about 1 g/cm$^3$, more preferably 0.4-0.9 g/cm$^3$, such as 0.42-0.78 g/cm$^3$. The inventive method is used to make particles of ORC having these specific aspect ratios directly from ORC materials, such as ORC fabric or non-wovens as characterized above utilizing the ball milling process. The particulates of the present invention have overall size (largest dimension) less than 500 microns, such as less than 300, 200, and less than 100 microns.

The low aspect ratio (1-20) particles should comprise the majority of the particles constituting the powdered material, i.e. over 50%, such as over 80% or over 90% of particles. The particulates having overall size (largest dimension) less than 500 microns, such as less than 300, 200, and less than 100 microns should comprise the majority of the particles constituting the powdered material, i.e. over 50%, such as over 80% or over 90% of particles.

In another aspect of the present invention, the product resulting from the ball-milling process comprising low aspect ratio and high tapped density particles of ORC are shown to have superior hemostatic or blood clotting properties.

ORC is an absorbable hemostatic material known to these skilled the art. A number of methods are known for forming various types of hemostats based on oxidized cellulose materials into powder, woven, non-woven, knit, and other forms and combinations thereof. Currently utilized hemostatic wound dressings include knitted or non-woven fabrics comprising oxidized regenerated cellulose (ORC), which is oxidized cellulose with increased homogeneity of the cellulose fiber. Examples of such hemostatic wound dressings commercially available include SURGICEL® absorbable hemostat, SURGICEL® NU-KNIT® absorbable hemostat, SURGICEL® FIBRILLAR absorbable hemostat, or SURGICEL® SNoW™ absorbable hemostat; all available from Johnson & Johnson Wound Management Worldwide, a division of Ethicon, Inc., Somerville, N.J., a Johnson & Johnson Company.

In further embodiments of the present invention, the ball milled ORC particles can be combined with various additives to further improve the hemostatic properties, wound healing properties, and handling properties, utilizing additives known to these skilled in the art, including: hemostatic additives, such as gelatin, collagen, cellulose, chitosan, polysaccharides, starch, CMC, calcium salts; biologics based hemostatic agents as exemplified by thrombin, fibrinogen, and fibrin, additional biologics hemostatic agents include, without limitation, procoagulant enzymes, proteins and peptides, each such agent can be naturally occurring, recombinant, or synthetic, and may be further selected from the group consisting of fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, albumin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combination thereof. Preferred biologic hemostatic agents that can used in combination with the ball-milled ORC particles are thrombin, fibrinogen and fibrin; Anti-infective agents, such as chlorhexidine gluconate (CHG), triclosan, silver, and similar anti-bacterial/microbial agents that are known in the art; and additives that increase the stickiness of the hemostat; diluents, saline solutions, and similar additives that known in the art.

For the purposes of the present disclosure, the aspect ratio of powder is defined as average aspect ratio of particles comprising the powder, with the aspect ratio of particles determined by a measurement of the longest dimension of the particle (length) divided by the shortest dimension of the particle (width), as visible under appropriate magnification under SEM or optical microscope. The lowest aspect ratio (AR) of 1 corresponds to a round particle, having longest dimension equal to the shortest dimension. An aspect ratio of about 20 corresponds to a fibrous particle having length 20 times diameter. The aspect ratios of experimental samples were determined by SEM imaging. Preferred aspect ratios according to the present invention are from 1 to 20, more specifically from about 1.5 to about 17.5.

The flowability of hemostatic particles is a parameter that influences the deployment of powders during surgical procedures. High flowability is preferred in a surgical setting for ease of deployment. Bulk density is the ratio of the mass of an untapped powder sample and its volume including the contribution of the interparticulate void volume. Tapped density is a measure of increased bulk density of powder that is obtained by mechanically tapping a container of the powder. Tapped density appears to be correlated with flowability. High tapped density is preferred for ease of deployment and mixing. Preferred tapped density is from about 0.35 to about 1 g/cm$^3$, more preferably 0.4-0.9 g/cm$^3$, such as 0.42-0.78 g/cm$^3$. Tapped density, for purposes of this application except as otherwise noted, is measured using a modified USP 616 method in which one (1) gram of powder is introduced into a dry graduated cylinder of 10 mL, and manually tapped with 100 taps for approximately 2 minutes.

The expression force for hemostatic powders is also an important parameter related to deployment of powders or paste during surgical procedures. The effort required to expel a liquid from a syringe, and to draw liquid into the syringe, are known as the expression force and aspiration force respectively. The expression force measure, however, is a more critical for dual-syringe mixing devices.

Dual-syringe mixing devices produce a substantially homogenously paste mixture by combining initially separate liquid and solid carriers and then passing the blended contents back and forth between two connected syringes via interconnected outlets. Therefore, a low expression force for dispensing the paste from a syringe is preferred for ease of mixing and ultimately for deployment of the resulting paste. The desired expression force is less than 1.51 lbf at the similar aspect ratio as seen in Table 3 when the $1^{st}$ or $2^{nd}$ 0.1 mL of paste is expressed using sterile Beckton Dickinson [male luer lock 1 mL syringes.

The optimal combination of properties was surprisingly found to be achievable by ball milling ORC but could not be achieve by shredding alone. One of the preferred ball milling methods is described as the follows. 50 g of pre-trimmed SURGICEL fabric (4"×4") was ball milled with 12 high-density Zirconia (zirconium dioxide $ZrO_2$, 20 mm in diameter; Glen Mills Inc., Clifton, N.J., USA) by placing the balls and the samples in a 500 mL grinding jar. The jar can be clamped into the latching brackets and then counterbalanced on the planetary ball mill PM100; Retsch, Inc., Newtown, Pa., USA). The milling was then performed bi-directionally at 300 rpm for 30 minutes, and then stopped for 1 hour for cooling at room temperature. Repeated the process as needed.

ORC samples can be ball milled with 5-30 or more high-density $ZrO_2$ balls, such as 12 $ZrO_2$ balls (20 mm in diameter; Glen Mills Inc., Clifton, N.J., USA) by placing the balls and the samples in a grinding jar (250 mL; 500 mL or larger). The jar can be clamped into the latching brackets and then counterbalanced on the mill (such as planetary ball mill PM100; Retsch, Inc., Newtown, Pa., USA). The milling can be then performed at 150-500 rpm, e.g. at 300 rpm for 5-60 minutes, such as for 10-30 min.

Other methods of generating compacted ORC powders of high density and low aspect ratio besides ball milling can be utilized. Rolling compaction refers to the continuous compaction of powders by roll mills. The powder is usually delivered by feed screw to rolls and densified by the pressure and shear force. Roll compaction is a powder agglomeration process used in variety of industries including the pharmaceutical, mineral and chemical industries. Roll compaction of poor flowability powder mixtures requires screw feed of the powder between two counter-rotating rolls. These then draw the powder into the compaction zone and apply a high pressure forming a strip of compacted powder. Powders compacted to such strips or ribbons by pressure between two-counter rotating rolls are then further milled into granules of low aspect ratio. In the present invention, woven or non-woven ORC material, or shredded or ball milled ORC material can be further roller compacted to reach desired low aspect ratios and high density ORC particles.

A hammer mill is another method that can be used to make an ORC particle having sufficient low aspect ratio and high tapped density. A hammer mill operates by impact action and will pulverize most dry, free-flowing materials. Material is fed into the hammer mill from the top and then falls into the grinding chamber. The material is contacted by a series of hardened steel hammers rotating at high speed. The material is ground by repeated contact with these hammers, contact with the walls of the grinding chamber, and particle to particle contact. The material remains in the hammer mill grinding chamber until the particles become small enough to escape by passing through the perforated screen that covers the bottom half of the grinding chamber.

A hammermill is essentially a steel drum containing a vertical or horizontal rotating shaft or drum on which hammers are mounted. The hammers are free to swing on the ends of the cross, or fixed to the central rotor. The rotor is spun at a high speed inside the drum while material is fed into a feed hopper. The material is impacted by the hammer bars and is thereby shredded and expelled through screens in the drum of a selected size. The hammer mill can be used as a primary, secondary, or tertiary crusher, i.e. ORC can be hammer milled from woven or non-woven material ORC source, or from shredded or ball milled ORC material. The main difference between cutting (shredding) and ball milling and other compacting/milling processes is the crushing mechanical impaction without sharp blades which is utilized in the ball milling and other compaction processes. Due to absence of sharp blades, the particles acquire different properties in terms of particle shape, surface, tapped density, etc. which are distinct from shredded (i.e. milled utilizing blades) particles.

The present invention has been described generally above. The following non-limiting examples provide additional details.

Example 1

Preparation of Compacted Powders Comprising ORC-Ball-Milled Powders (BMP)

Several pieces of 4"×4" pre-trimmed non-sterile SURGICEL® fabric (ETHICON, Inc., Lot #7A8654), were vacuumed dried for 24 hours prior to milling. The total weight of samples was 6 grams. Samples were then mixed with 12 high-density $ZrO_2$ balls (20 mm in diameter; Glen Mills Inc., Clifton, N.J., USA) and sealed in a 250 mL grinding jar. The jar was clamped into the latching brackets and then counterbalanced on the mill (planetary ball mill PM100; Retsch, Inc., Newtown, Pa., USA). Milling was performed at 300 rpm for 10 min. The milled powder then was dried in a vacuum oven (Fisher Scientific Model 280A Isotemp vacuum oven) with a vacuum pump (LabCare America Pump PV-35) at 65° C. for 2.5 h. The milled powder was finally stored in a nitrogen box.

50 grams of non-sterile SURGICEL® fabric (Ethicon, Inc., Lot#7A86S4), which was kept in a nitrogen box, was pre-cut into 4"×4" size and vacuum-dried for 24 hours before the milling process. Samples were mixed with 12 high-density $ZrO_2$ balls (20 mm in diameter; Glen Mills Inc., Clifton, N.J., USA) and then sealed in a grinding jar (capacity: 500 mL). The jar (total mass=~7.4 kg) was clamped into the latching brackets and then counterbalanced on the mill (planetary ball mill PM100; Retsch, Inc., Newtown, Pa., USA, SN: 128081207H). The milling was performed at 300 rpm for 30 minutes with same rotation. Milled ORC powder was removed from the grinding jar and dried in a vacuum oven (Fisher Scientific Model 280A Isotemp vacuum oven) and a vacuum pump (LabCare America Pump PV-35) at 65° C. for 2.5 hours.

In addition, ORC-based SURGICEL®NU-KNIT® absorbable hemostat was utilized in preparing the powders of this invention, using the same methods as described above.

Analysis of optical microscope and SEM images shows that with longer time of ball milling the resulting BMP particles transition from elongated high aspect ratio (>10) structures to more and more rounded aggregates having aspect ratios closer to 1.

Referring now to Table 1, temperature data collected during ball milling process are shown with readings taken throughout the ball milling process. The data indicates that there was only a limited temperature increase, with the maximum temperature of 38° C. recorded after 30 minutes of ball milling, which was well sufficient for obtaining BMP of low aspect ratios.

TABLE 1

Temperature vs. Time

| | Ball Milling time | | | | | |
|---|---|---|---|---|---|---|
| | 0 min | 3 min | 6 min | 10 min | 20 min | 30 min |
| Temperature* | 22.2° C. | 22.3° C. | 22.3° C. | 23.0° C. | 30.5° C. | 38.0° C. |

*Temperature was obtained when the IR temperature detector was placed on the top of the open grinding jar with samples and $ZrO_2$ balls.

Roller-Compacted ORC Powder

Shredded ORC powders were obtained by shredding ORC fabric through a Fitz Mill equipped with a screen mesh 1726-150. The raw bulk density and tapped density were 0.2 g/mL and 0.26 g/mL, respectively, measured with a standard USP 616. The shredded ORC powders were fed into a roller compactor (WP 120×40V, #900-0071, Alexanderwerk, Inc, PA). 5 Liter high flow hopper with helical band screw mounted horizontally above feed screw inlet. High output feed screw with reliefs for friction pins. Single helix in hopper inlet and double helix in the vacuum area were towards the front of the feeding screw. A Vacuum de-aeration filter pipe (<1 um) was installed around the feed screw for removing entrained air before the rollers. The sample flew well enough to achieve a flake of 2.2-2.7 mm. Higher pressure was required to force the fibers to break around 180 bars, 16.2 Kn cm of roller width. The pressure was around 6 Kg/hour for the procedure of feed screw transportation in order to move the sample smoothly. Standard rotor angle starting with a 1.25 mm screen for coarse breaking and a 0.63 mm screen for the fine granulation. Round screens (1.25 mm round) were used to start and then 0.80 mm square screens were used for more aggressive shear. After compaction, samples were sieved through a screen sieves set of 80, 100, 120, 140, 170, 230, and 270 meshes, with a amplitude-modulated ATM sonic sifter for 5 minutes. The particle distributions were 31.1% (>180 micons), 0.7% (>150 micons), 0% (>125 micons), 0.1% (106 micons), 3.6% (90 micons), 20.2% (63 micons), 5% (53 micons), and 37.6% in the bottom pan. Except for the sample (>180), the rest of the sieved samples were in fiber formats. The aspect ratio and tapped density of the sample (>180 micons) were approximately 1.5 and 0.44 g/mL, respectively.

For comparative purposes, shredded/chopped ORC powder was prepared from the same starting ORC fabric as follows. A quantity of ORC fabric was placed into a shredder (FitzMill, Fitz Patrick Company, IL, USA), processed at speed of 6000 rpm. The shredded ORC powder was obtained with a FitzMill mesh 1726-080 screen. Further sieving and/or varying of the time of shredding resulted in making shredded/chopped ORC powders of varying aspect ratios for comparative purposes.

Example 2

Physical Characterization of Compacted ORC Powders or Ball-Milled Powders (BMP)

Figure 2:
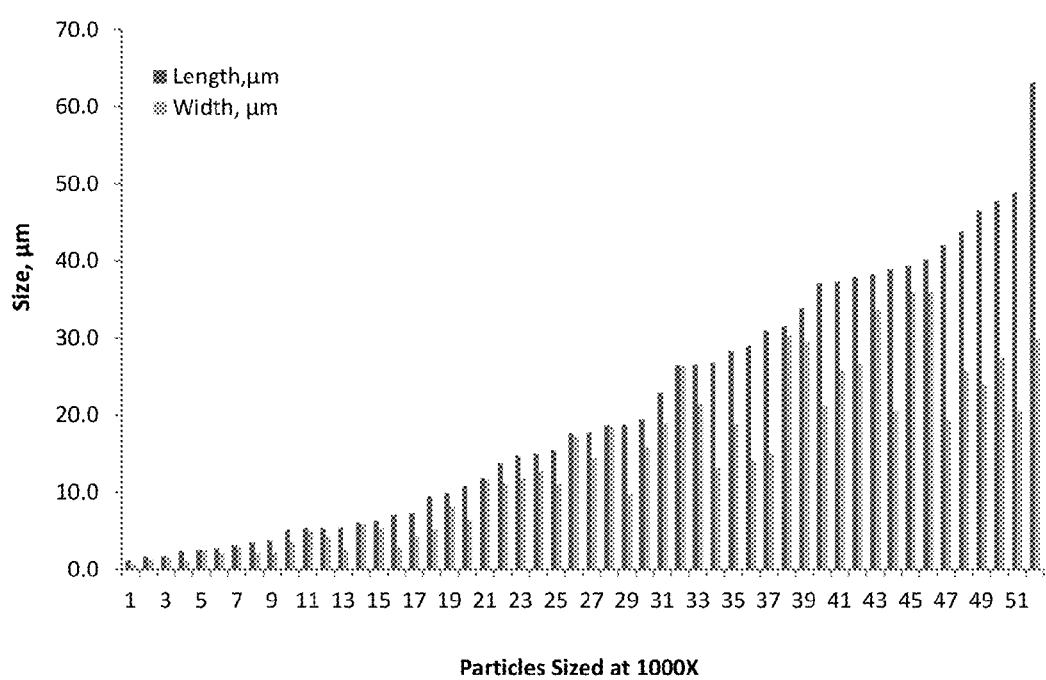
FIG. 2 is a graph of particle size distribution of ball milled material as measured by SEM.

For further characterization, BMP was stirred and mixed in a sonic mixer for 3 minutes in 99% isopropanol. After drying, both BMP and shredded ORC powder (comparative example) were characterized by scanning electron microscope (SEM) and dynamic light scattering (DLS). DLS analysis indicated that the range of particle sizes for BMP was from about 1.75 micrometer to 116 micrometers with a median length of 36 micrometers. Dynamic SEM photos were imported into a drafting program (by Horiba Instruments, Inc) and 103 particles were measured for length and width. The majority of particles exhibited an aspect ratio (L/W) between 1.0-2.5. Comparison of FIGS. 1 and 2 show that the measurements of by different techniques indicate generally the same trends and the measurements by SEM are in agreement with the DLS data.

An SEM analysis of shredded/chopped ORC powder is shown for comparative purposes. This powder is similar to powder described in U.S. Patent Application publication 2006/0233869 by Looney et al., which is incorporated by reference herein for all purposes in its entirety, which had the average aspect ratio length (L) to width (W) of about 30 (W: 15 um; L: 35-860 nm). The average aspect ratio of ball milled Surgicel powder is about 20 times smaller than chopped Surgicel fiber (obtained with FitzMill 1726-080 mesh screen). The tapped density of BMP (0.78 g/mL) is about 3 times greater than the tapped density of chopped Surgicel (0.26 g/mL).

Comparative Example

Shredded ORC powder was made having substantially the same aspect ratios as the inventive ball milled powders. The shredded ORC powders were obtained by shredding ORC fabric through a Fitz Mill at 6000 rpm and equipped with a screen mesh followed by sieving through a screen sieves set of 45, 80, 120, 400, with a sieve shaker (W.S. Tyler, OH, USA, Model: RX-29, SN: 10-1046). Aspect ratio characterizations were performed using optical measurement technique as described above.

Example 3

Effects of Particles Aspect Ratio on Tapped Density and Flowability: BMP Vs. Shredded/Chopped Powders Particle flowability was measured using a modified USP 1174 method—Powder flow. Four digits of Scale (Mettler Toledo Excellent XS204, ETHICON BA-046) was used to measure the weight of the powder as it traveled through a glass tube (OD: 0.8 cm, ID: 0.6 cm, length: 31 cm). The flow rate of powder was determined by the travel time and total travel distance (40 cm).

Referring now to Table 2, a comparison is presented of tapped density and flowability of shredded ORC powders and BMP. Analysis of the data indicates that at substantially the same or similar aspect ratios, BMP exhibit higher tapped density and much better flowability relative to shredded powders. High flowability and tapped density of BMP at the lowest aspect ratios cannot be obtained with shredded powders of any aspect ratios.

TABLE 2

Comparison of Tapped Density and Flowability of ORC powders

| Ball Milled ORC Powder | | | Shredded ORC Powder | | |
|---|---|---|---|---|---|
| Aspect Ratio | Tapped Density (g/cm$^3$) | Flowability (cm/sec) | Aspect Ratio | Tapped Density (g/cm$^3$) | Flowability |
| 1.5 | 0.78 | 200 | 1.9 | 0.65 | 59.2 |
| 4.8 | 0.67 | 70.6 | 3.2 | 0.58 | 44.2 |
| 8.7 | 0.53 | 17.4 | 9.9 | 0.41 | 7.55 |
| 17.5 | 0.46 | 7.6 | 17.7 | 0.3 | 3.24 |
| 20.9 | 0.42 | 5.9 | 23.7 | 0.24 | 3.12 |
| 36 | 0.18 | 1.6 | 37.4 | 0.12 | 1.37 |

Example 4

Effects of Particles Aspect Ratio on Blood Clotting: BMP Vs. Shredded/Chopped Powders The inventive BMP and shredded ORC powders prepared as a comparative example, each having varying aspect ratios were prepared as described above with longer time of milling or shredding resulting in lower aspect ratios. The average aspect ratio for each sample was determined by SEM.

The blood clotting effects of these powders was then experimentally tested in-vitro as follows. Fresh porcine blood from a 4 month-old female porcine (45 Kg) was collected in several 4.5 mL BD Vacutainers with a 3.2% buffered sodium citrate solution. The blood was then diluted with saline solution (0.9% NaCl USP, Lot#082420, Baxter Healthcare) with a ratio of 1/1 (v/v). An ST4 Coagulation Analyzer was used to determine the in-vitro blood clotting time. Each cuvette contained 200 uL of diluted blood followed by the application of 2 mg of each test article. Each sample was tested in triplicate.

Figure 3:
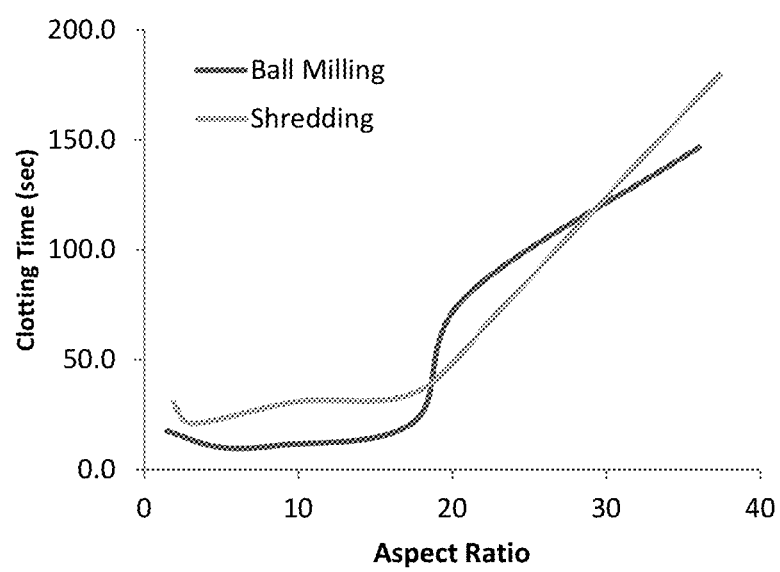
FIG. 3 is a graph of the results of in-vitro blood clotting testing shown as clotting time versus aspect ratio for shredded and ball milled ORC powders.
Figure 4:
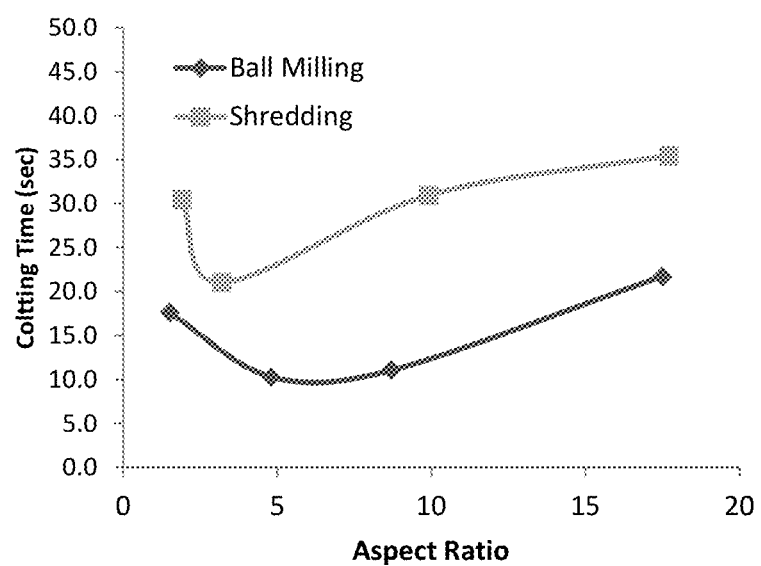
FIG. 4 is a graph of in-vitro blood clotting testing shown as clotting time versus aspect ratio for shredded and ball milled ORC powders.

Referring now to FIGS. 3 and 4, the results of the testing shown as clotting time vs. aspect ratio for shredded ORC powders and BMP. FIG. 4 shows the same data as FIG. 3 but for a narrow range of aspect ratios. Analysis of data presented indicates that at low aspect ratios, particularly at aspect ratios from about 1 to about 18, BMP exhibit much better blood clotting relative to shredded ORC powders, with up to 3 times faster time to clotting at some aspect ratios.

Example 5

Effects of Particles Aspect Ratio on ORC Paste Expression Force: BMP Vs. Shredded/Chopped Powders Materials and methods used were as follows. 0.095 grams of ORC powder with different aspect ratios (AR) were pre-filled in a Beckton Dickinson male luer lock 1 mL syringe. The sample was connected with an adapter and pre-mixed with another Beckton Dickinson male luer lock syringe pre-filled with 0.2 mL saline [0.9 NaCl (aq)] with back-and-forth passes for 20 times, followed by sitting for 30 seconds to allow for full hydration. The expression force of the paste was determined by the Instron (model: 5544) and a load cell (LC-105). The expression force was recorded for the first 0.1 mL of expressed solution and then for the second 0.1 mL of the expressed solution and the results are shown in Table 3. At lower aspect ratios, from about 1 to about 5, shredded ORC powders were not mixable with saline and could not be expressed from the syringe within the device load limits. On the contrary, BMP powders were mixable and dispensed from the syringe with a force of less than 1.51 lbf at the similar aspect ratio.

TABLE 3

Expression forces for various aspect ratios of powders

| Method of Making Powder | Aspect Ratios | Expression Force* (lbf) 1st 0.1 mL | Expression Force* (lbf) 2nd 0.1 mL | Aspect Ratios | Expression Force* (lbf) 1st 0.1 mL | Expression Force* (lbf) 2nd 0.1 mL |
|---|---|---|---|---|---|---|
| BMP | 4.8 | 0.37 | 1.51 | 1.5 | 0.43 | 0.30 |
| Shredded ORC | 3.2 | 1.47 | 9.73** | 1.9 | 3.66 | 9.18** |

*Maximum load (lbf);
**The measurement was stopped due to the force reaching closely to the maximum limit of the load cell. The average expression force of 1st 0.1 mL saline: 0.23 lbf.

Example 6

In Vivo Hemostasis Study: BMP Vs. Controls

The time to hemostasis (TTH) was evaluated in the following swine biopsy punch spleen model for controls, including Surgicel Original, Fibrillar, SURGIFLO® Hemostatic Matrix mixed with saline (SURGIFLO/saline) and SURGIFLO® Hemostatic Matrix mixed with thrombin (SURGIFLO/thrombin) and for inventive materials which included BMP, as well as BMP Plus (BMP is a powder made of SURGICEL® fabric by ball milling as described above. BMP Plus is a powder made of SURGICEL® fabric mixed with carboxymethyl cellulose (CMC) and calcium citrate by ball milling as described above. SURGIFLO® Hemostatic Matrix is commercially available from Johnson & Johnson Wound Management Worldwide, a division of Ethicon, Inc., Somerville, N.J., a Johnson & Johnson Company.

Biopsy punch incisions (6 mm long and 3 mm deep) were made on a swine spleen. Referring now to Table 4, seven test articles, including gauze as a negative control, were applied to the wounds, separately, with number of each test repeated ten times (N=10). Tamponade was applied for 30 seconds followed by a 30-second observation. When hemostasis was not achieved, additional tamponade was applied to stop the bleeding. Pieces of surgical gauze were used as negative controls.

TABLE 4

Test articles for hemostatic efficacy study

| Test Article | Size/Dimension/Description | N |
|---|---|---|
| BMP | 0.15 g Ball milled Surgicel fabric powder | 10 |
| BMP Plus | 0.15 g; ball-milled SURGICEL/CMC/calcium citrate with the ratio of 100/10/1 by weight | 10 |

TABLE 4-continued

Test articles for hemostatic efficacy study

| Test Article | Size/Dimension/Description | N |
|---|---|---|
| Fibrillar-Positive Control | 0.15 g | 10 |
| SURGICEL Original-Positive Control | 0.15 g; a four 2.5 × 2.5 cm pieces, stacked and applied simultaneously | 10 |
| SURGIFLO/2 mL saline - Positive Control | 1 mL of mixture | 10 |
| SURGIFLO/ 2 mL thrombin- Positive Control | 1 mL of mixture; SURGIFLO mixed with 2 mL human thrombin | 10 |
| Gauze-Negative Control | A non-sterile 4" × 4", 8-ply, folded over upon itself 3 times before applied to the wound site | 10 |

Figure 5:
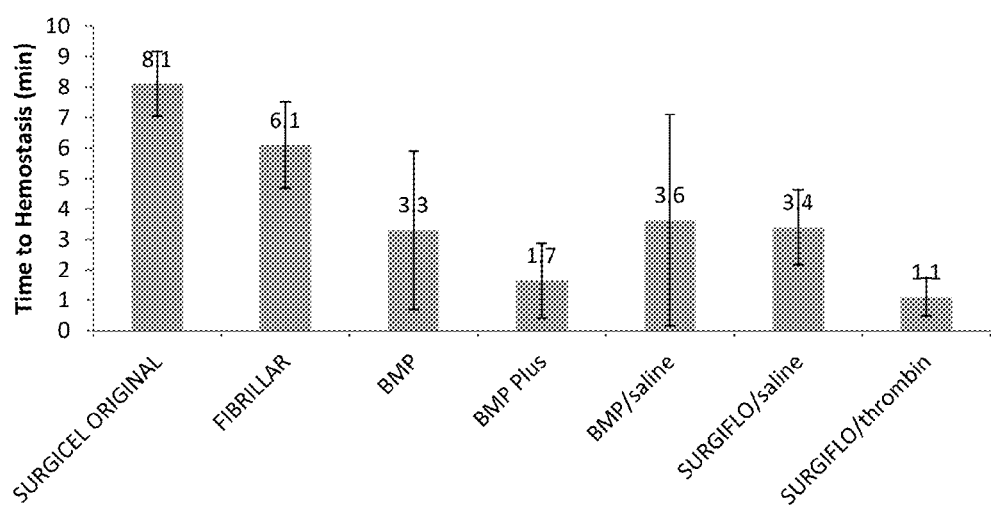
FIG. 5 is a graph of the time to hemostasis for several different powders.

The results of the hemostatic study are presented in FIG. 5. TTHs of BMP and BMP Plus were faster than Surgicel Original and Fibrillar (positive controls). In addition, BMP Plus, showed a faster TTH than BMP in a biopsy punch model. TTH of BMP Plus was as good as Surgiflo/thrombin (average TTH: within 2 minutes). Analysis of the data presented indicates good hemostatic properties of the BMP and BMP Plus of the current invention.

Example 7

Viscosity Characterization

BMP was prepared as described above (Example 5) and utilized for making paste. To each 6 mL syringe, 1 gram of BMP was added. The plunger was pre-positioned to 2.2 mL. The syringe was then mixed with 2 mL of sterile saline by connecting to another syringe and transferring the BMP/saline mixture back and forth between the syringes, with 10 transfers to reach ready-to-use consistency. Additional transfers were applied if necessary. Concentrations of 1 gram/1.6 mL, 1 gram/1.8 mL, 1 gram/2 mL and 1 gram/2.2 mL were evaluated; however, the first two concentrations of samples were very difficult to mix and gel block was found in the syringes. Concentration of 1 gram per 2.2 mL was too dilute compared to 1 gram/2 mL. The data presented corresponds to 1 gram/2 mL. Commercially available SURGIFLO® Hemostatic Matrix (Control) was mixed with 2 mL of sterile saline.

Figure 6:
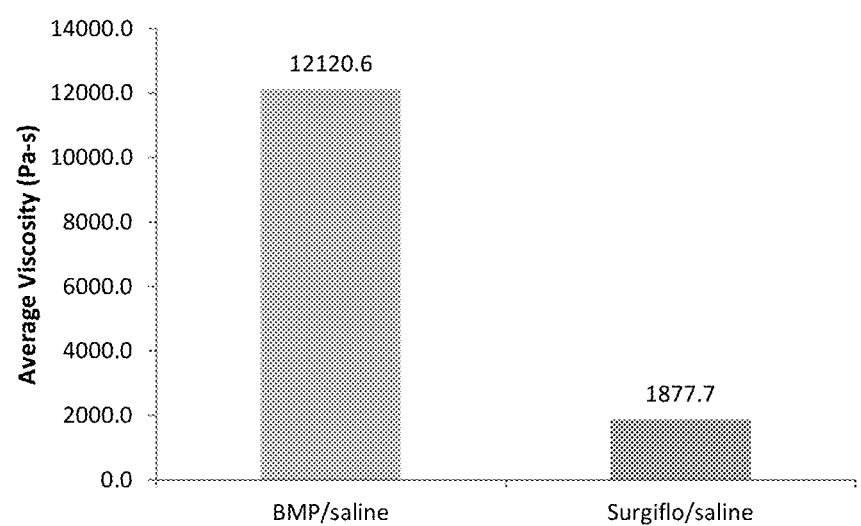
FIG. 6 is a graph showing average viscosity of flowable materials.

Viscosity was measured throughout the syringe: beginning (0-1 mL). Viscosity was measured with a controlled-strain rotational rheometer (ARES, TA Instrument Inc.) equipped with a Peltier temperature controller. Each mixed sample was sandwiched between a 25-mm parallel plate and the Peltier plate surface. The gap between the two plates was set to 1.25 mm for all measurements. Dynamic time sweep test with strain=1%, frequency=1 rad/s and temperature=25° C. were used for all measurements. The first measured data point was reported as the viscosity of sample. Triplicate measurements were performed and the results are reported in FIG. 6. The viscosity of flowable BMP based paste is over six times higher than the viscosity of the Surgiflo. Higher viscosity can be useful in treating certain types of bleeding.

Example 8

In Vivo Hemostasis Study: ORC Paste Vs. Controls

The time to hemostasis (TTH) was evaluated in the following swine biopsy punch spleen model. Biopsy punch incisions (6 mm long and 3 mm deep) were made on a swine spleen. Tamponade was applied for 30 seconds followed by a 30-second observation. Referring now to the concentrations of the test articles prepared as follows. Nine test articles were applied to the wounds, separately, with number of each test repeated ten times (N=10). When hemostasis was not achieved, additional tamponade was applied to stop the bleeding. Pieces of surgical gauze were used as negative controls. The results are reported in FIG. 7. The applied amount of each test article in powder format and in paste format is 0.2 g and 1 ml, separately. Table 5 lists all the test articles.

TABLE 5

Test articles for hemostatic efficacy study

| Test Article | Sample Description | N |
|---|---|---|
| BMP/saline | 1 g BMP mixed with 2 ml saline | 10 |
| BMP/CMC/Ca2+/saline | 1 g of BMP/CMC/calcium citrate (87:8.7:4.3%, w/w) mixed with 2 ml saline | 10 |
| BMP/CMC/saline | 1 g of BMP/CMC (87:8.7%, w/w) mixed with 2 ml saline | 10 |
| Ca2+/saline | calcium citrate (4.3%, w/w) in 2 m saline | 10 |
| BMP/Ca2+/saline | 1 g of BMP/calcium citrate (87:4.3%, w/w) mixed with 2 ml saline | 10 |
| BMP | BMP alone | 10 |
| BMP/CMC | BMP mixed with CMC (87:8.7%, w/w) | 10 |
| BMP/Ca2+ | BMP mixed with calcium citrate (87:4.3%, w/w) | 10 |
| BMP/CMC/Ca2+ | BMP, mixed with CMC and calcium citrate (87:8.7:4.3%, w/w) | 10 |
| Gauze-Negative Control | A non-sterile 4" × 4", 8-ply, folded over upon itself 3 times before applied to the wound site | 10 |

BMP was prepared as described in Example 5.

Figure 7:
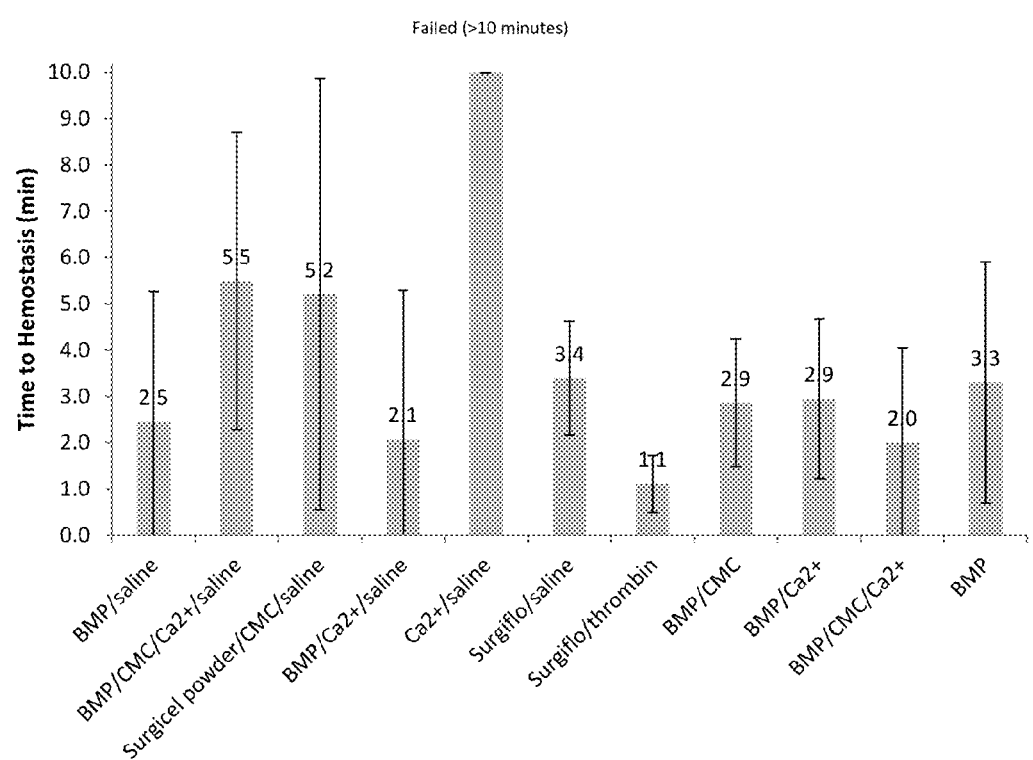
FIG. 7 is a graph of hemostatic efficacy study: time to hemostasis (TTH) of flowable paste and Surgical powder with additives in spleen biopsy punch model (n=10).

Data for hemostatic efficiency is shown in FIG. 7, which indicates that BMP based powders and paste (mixture of BMP with normal saline) has good hemostatic properties. BMP/$Ca^{2+}$/saline and BMP/CMC/$Ca^{2+}$ had excellent hemostatic efficacy. The TTH of 10 minutes for $Ca^{2+}$ corresponds to a test that failed to achieve hemostasis and was assigned TTH=10.

Example 9

In Vivo Hemostasis Study: BMP Powder Vs. Other Powders

Figure 8:
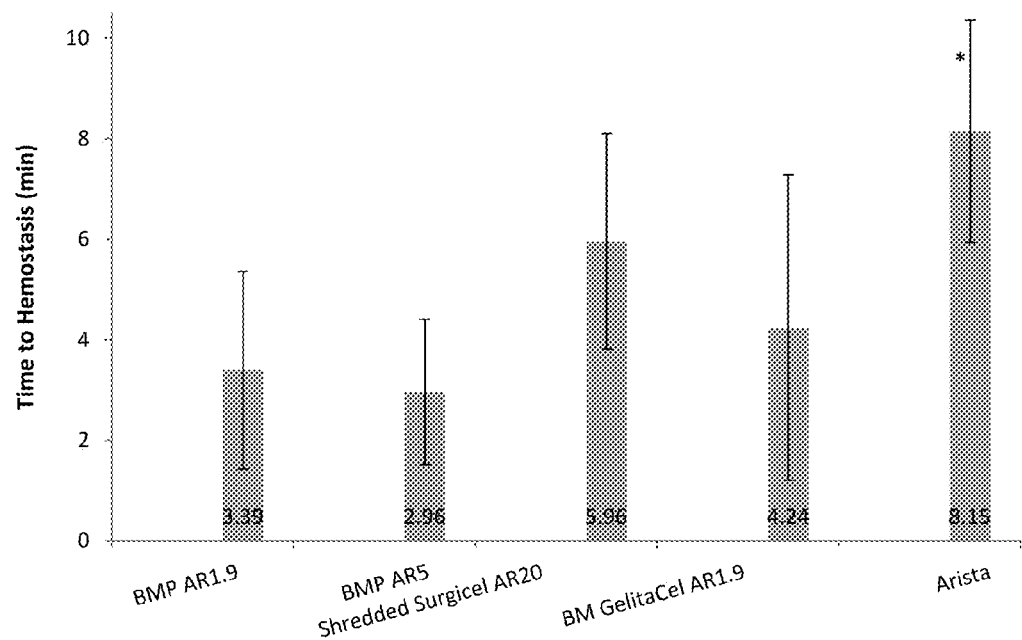
FIG. 8 is a graph of hemostatic efficacy study-time to hemostasis (TTH) of various materials in a spleen biopsy punch model.

Hemostatic efficacy of BMP with different aspect ratios vs. oxidized cellulose powder (ball-milled GelitaCel powder) and starch based powder (Arista) are compared in FIG. 8. The method of making those powders is described below. 6 grams of SURGICEL® fabric (Ethicon, Inc.) was pre-cut into 4"×4" size and vacuum-dried for 24 hours before the milling process. Samples were mixed with 12 high-density $ZrO_2$ balls (20 mm in diameter; Glen Mills Inc., Clifton, N.J., USA) and then sealed in a grinding jar (capacity: 250 mL). The jar (total mass=~4.6 kg) was clamped into the latching brackets and then counterbalanced on the mill (planetary ball mill PM100; Retsch, Inc., Newtown, Pa., USA, SN: 128081207H). The milling was performed at 300 rpm for 3.510 minutes with same rotation. Milled ORC powder was removed from the grinding jar and dried in a vacuum oven (Fisher Scientific Model 280A Isotemp vacuum oven, SN: 1507060671168) and a vacuum pump (LabCare America Pump PV-35, SN: 301090011) at 65° C. for 2.5 hours. The resulting BMP was kept in a nitrogen box. The aspect ratios of samples were determined by SEM. By using same grinding parameters, the milled GelitaCel powder with aspect ratio of 1.92 required 2-hour grinding process. Analysis of the data presented in FIG. 8 indicates that BMP exhibited better hemostatic efficiency relative to the comparative powders at the same aspect ratios of the powders. The SURGICEL® powder AR 20 data point on the plot FIG. 8 corresponds to the shredded ORC powder (comparative example).

We claim:

1. A hemostatic material comprising a roller compacted ORC powder comprising particles having average aspect ratio from about 1 to about 18 having a particle size greater than 180 micron and tapped density of at least 0.44 g/mL.

2. The hemostatic material of claim 1, wherein said material further comprises an additive, wherein said additive is CMC or other polysaccharides, calcium salt, anti-infective agent, hemostasis promoting agent, gelatin, collagen, or combinations thereof.

3. A hemostatic paste comprising the hemostatic material according to claim 1 and a saline solution.

4. The hemostatic paste of claim 3, wherein the paste has a viscosity of over 10000 Pa-s.

5. The hemostatic material of claim 1, wherein said powder having flowability of at least 7.5 cm/s.

6. A method of making the hemostatic material of claim 1 comprising the steps of:
introducing an ORC-based material into a roller compaction device;
compacting the ORC-based material into a powder, until said powder reaches an aspect ratio of from about 1 to about 18.

7. The method of claim 6, wherein said ORC material is ORC fabric, ORC non-woven, or shredded ORC material.

8. The method of claim 6 further comprising the step of mixing the ORC material with an additive, wherein said additive is CMC, calcium salt, anti-infective agent, hemostasis promoting agent, gelatin, collagen, saline, or combinations thereof.

9. A method of treating a wound comprising the steps of applying the hemostatic powder of claim 1 onto and/or into the wound of a patient.

* * * * *